United States Patent [19]

Kira

[11] Patent Number: 4,725,273

[45] Date of Patent: Feb. 16, 1988

[54] ARTIFICIAL VESSEL HAVING EXCELLENT PATENCY

[75] Inventor: Kazuaki Kira, Kobe, Japan

[73] Assignee: Kanegafuchi Kagaku Kogyo Kabushiki Kaisha, Osaka, Japan

[21] Appl. No.: 897,970

[22] Filed: Aug. 20, 1986

[30] Foreign Application Priority Data

Aug. 23, 1985 [JP] Japan .................................. 60-186050
Sep. 12, 1985 [JP] Japan .................................. 60-202411

[51] Int. Cl.$^4$ .............................................. A61F 2/06
[52] U.S. Cl. .......................................... 623/1; 623/12; 623/66; 521/905; 521/916
[58] Field of Search ............... 623/1, 66, 12; 521/62, 521/63, 905, 916

[56] References Cited

U.S. PATENT DOCUMENTS

| | | | |
|---|---|---|---|
| 4,173,689 | 11/1979 | Lyman et al. | 521/64 |
| 4,208,745 | 6/1980 | Okita | 623/1 |
| 4,254,180 | 3/1981 | Kline . | |
| 4,286,341 | 9/1981 | Greer et al. | 623/1 |
| 4,355,426 | 10/1982 | MacGregor | 623/1 |
| 4,499,211 | 2/1985 | Walch et al. | 521/62 X |
| 4,524,155 | 6/1985 | Walch et al. | 521/62 X |
| 4,550,447 | 11/1985 | Seiter, Jr. et al. | 623/1 |
| 4,553,272 | 11/1985 | Mears | 623/1 |
| 4,657,544 | 4/1987 | Pinchuk | 623/1 |
| 4,661,530 | 4/1987 | Gogolenski et al. | 521/62 X |

FOREIGN PATENT DOCUMENTS 0117072  8/1984  European Pat. Off. .
0130401  1/1985  European Pat. Off. ............... 623/1

*Primary Examiner*—Richard J. Apley
*Assistant Examiner*—Alan W. Cannon
*Attorney, Agent, or Firm*—Armstrong, Nikaido, Marmelstein & Kubovcik

[57] ABSTRACT

An artificial vessel having an excellent patency, wherein the vessel wall is made of an elastomer having a porous structure and the contact surface with blood has pores with a mean diameter of from 1 to 100 $\mu$m and holes with a mean diameter of from 0.01 to 10 $\mu$m.

The artificial vessel may also be reinforced with tubular material made of fiber or with heat-set tubular material made of fiber so that the vessel has a stress-strain curve approximate to that of a vital vessel or the vessel can be subjected to sterilization by boiling or by high-pressure steam.

The artificial vessel has the porosity, contact surface with blood suited for encapsulation, and an excellent patency as well as a compliance approximate to that of a vital vessel.

5 Claims, 2 Drawing Figures

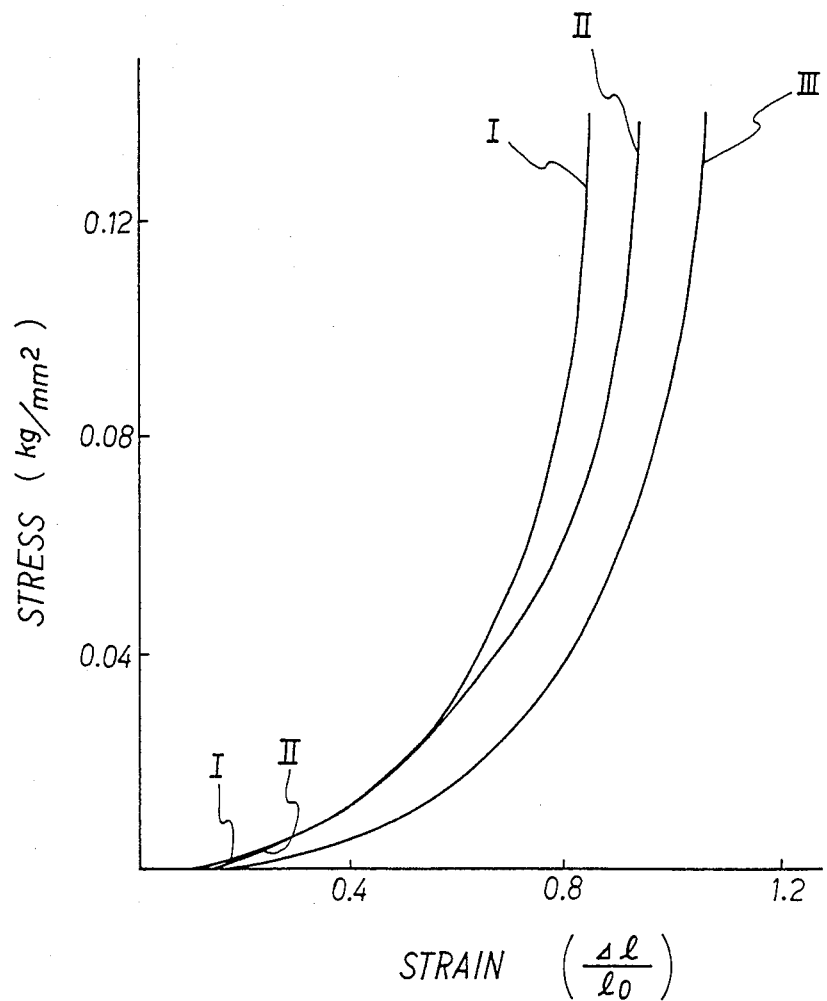

ARTIFICIAL VESSEL HAVING EXCELLENT PATENCY

BACKGROUND OF THE INVENTION

The present invention relates to an artificial vessel having an excellent patency. More particularly, the present invention relates to an artificial vessel having an excellent patency, wherein the vessel wall is made of an elastomer having a porous structure and the contact surface with blood has pores with a mean diameter of from 1 to 100 μm and holes with a mean diameter of from 0.01 to 10 μm.

In recent years, study on the artificial vessel has proceeded with progress in vascular surgery and many artificial vessels have been developed. Hitherto, for an artificial artery of a medium- or large-caliber with a diameter of about not less than 6 mm, the Debakey artificial vessel made of woven Dacron (USCI. Co., Ltd. of U.S.A.), the Gore-Tex vessel (Gore Co., Ltd. of U.S.A.) which is made of an expanded polytetrafluoroethylene (hereinafter referred to as "EPTFE"), and the like have been clinically used.

The above artificial vessels have pores which communicate the inside and the outside of the vessel wall. Soon after the artificial vessel is grafted into a living body, it is encapsulated to serve as the artificial vessel. Such property of having the communicating pores suited for encapsulation is hereinafter referred to as "porosity".

However, these artificial vessels have a disadvantage in that they have poor patency and thus cannot be clinically used as artificial veins or as artificial arteries of a small-caliber with an inner diameter of not more than about 6 mm. Therefore, a patient's own veins have hitherto been used in vascular reconstructive surgery of arteries below the knees or of the coronary arteries-aorta bypass.

In order to reduce the above disadvantage of an conventional artificial vessel and to obtain the artificial vessel having an excellent patency, it appears to be important for the artificial vessel to have a compliance approximate to that of a vital vessel and to have a contact surface with blood suited for encapsulation as well as to have a porosity suited for encapsulation.

The present inventor has already found that an artificial vessel wherein the vessel wall is made of an elastomer having a porous structure has a compliance approximate to that of a vital vessel, a porosity and a contact surface with blood both suited for encapsulation and an excellent patency, and have filed patent applications therefor (Japanese Patent Application No. 39077/1984, No. 39971/1984, No. 39972/1984, No. 44396/1984, No. 44397/1984, No. 44398/1984, No. 51768/1984, No. 52674/1984 and No. 99131/1984).

OBJECT OF THE INVENTION

In order to develop an artificial vessel having the above three important properties and even more excellent patency, the present invention is aimed at providing an aritificial vessel having a contact surface with blood particularly suited for encapsulation.

SUMMARY OF THE INVENTION

According to the present invention, there is provided an artificial vessel having an excellent patency, wherein the vessel wall is made of an elastomer having the porous structure and a contact surface with blood has pores with a mean diameter of from 1 to 100 μm and holes with a mean diameter of from 0.01 to 10 μm. The present invention was made from the finding that the patency of the artificial vessel can be improved when pores and holes having a specific mean diameter are present on the contact surface with blood.

BRIEF DESCRIPTION OF THE DRAWINGS

FIG. 2 is a graph of stress-strain curves of the carotid artery (curve I), the artificial vessel prepared in Example 3 (curve II) and the thoracic aorta (curve III), respectively.

DETAILED DESCRIPTION

Figure 1:
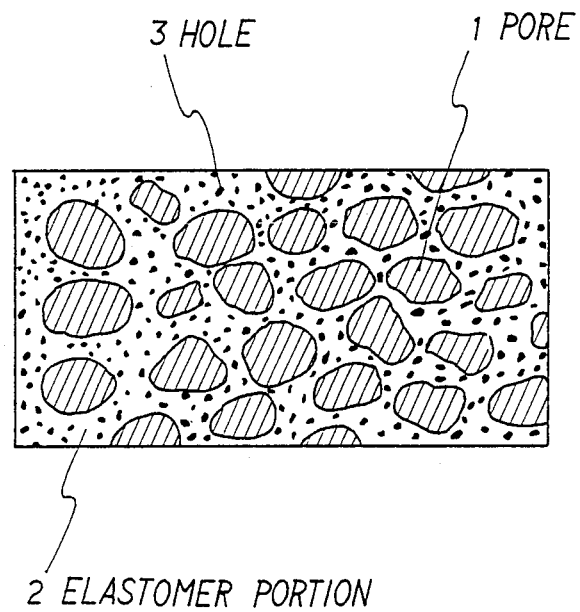
FIG. 1 illustrates the contact surface with blood of the artificial vessel of the present invention obtained in Example 1, observed with. a scanning type electron microscope.

In the present invention, the erm "the contact surface with blood" means the an inner surface of the artificial vessel, i.e. the surface of the vessel wall which is in contact with blood.

FIG. 1 is a sketch of the contact surface with blood of the artificial vessel of the present invention, observed by a scanning type electron microscope with mangification of about ×1000. As shown in FIG. 1, the contact surface with blood of the artificial vessel of the present invention comprises pores (1), an elastomer portion (2) surrounding pores (1), and holes (3) present in the elastomer portion (2).

The term "pores" in the present invention refers to a substantially bottomless structure such as a duct which passes through the vessel wall or a structure which is formed by linking of a hollow space present in the surface of the vessel wall with a vacant space in the vessel wall.

The term "holes" in the present invention refers to as a concave structure with a bottom.

The pores of the artificial vessel of the present invention have a mean diameter of from 1 to 100 μm, preferably from 5 to 50 μm, and more preferably from 10 to 30 μm. When the mean diameter is less than 1 μm, the encapsulation of the artificial vessel becomes poor, and when the mean diameter is more than 100 μm, blood flow is disturbed and antithrombogenicity of the artificial vessel is lowered.

The holes of the artificial vessel of the present invention have a mean diameter of from 0.01 to 10 μm, preferably from 0.1 to 5 μm, and more preferably from 0.5 to 3 μm. When the mean diameter is less than 0.01 μm, the holes do not function effectively for the encapsulation, and when the mean diameter is more than 10 μm, the strength of the contact surface with blood is decreased or non-uniform portion is formed by a combination of pores and holes, which results in a low antithrombogenicity.

The shape, distribution or number per unit area of the pores or of the holes, or ratio between the pore and the hole numbers are not particularly limited. The shape is preferably a round, oval, or similar form. The distribution is preferably such that the pores or the holes are substantially uniformly distributed in the contact surface with blood. The number per unit area is preferably from $0.1 \times 10^5$ to $20 \times 10^5/cm^2$, more preferably from $0.5 \times 10^5$ to $13 \times 10^5/cm^2$ for the pores, and preferably from $1 \times 10^5$ to $200 \times 10^5/cm^2$, more preferably from $10 \times 10^5$ to $150 \times 10^5/cm^2$, for the holes. The ratio of the pores/the holes in number is preferably from 1/1 to 1/1000, more preferably from 1/5 to 1/100.

The pores are supposed to serve as an anchor for pseudointima and neointima and to accelerate the rapid and stable encapsulation. The holes are supposed to improve the antithrombogenicity by reducing the elastomer area which is in contact with blood.

The above-mentioned size or shape of the pores or of the holes present in the contact surface with blood refers to the size or shape at the opening part thereof in the contact surface with blood. The mean diameter of the pores or of the holes was determined by measuring the maximum diameter of the pores or of the holes present per $2.5 \times 10^5$ cm$^2$ of the contact surface with blood and calculating the arithmetic mean.

The vessel wall of the artificial vessel of the present invention is made of an elastomer having a porous structure.

The porous structure of the elastomer contains pores which pass through the whole thickness of the vessel wall from the inner surface to the outer surface and has the porosity. The pores are formed by partitions, which are made of the elastomer and connected with each other continuously. Preferably, the partition itself contains a large number of small pores or holes so that the vessel wall has a more bulky structure and the artificial vessel having a compliance approximate to that of a vital vessel is obtained.

Particularly preferable as a porous structure is a network structure where the pores having a substantially uniform diameter are present over the entire thickness of the vessel wall from the inner surface to the outer surface.

Since the vicinity of the inner surface and of the outer surface of the vessel wall has a slightly more condensed structure than the rest which is between the vicinity of the inner and the vicinity of the outer surface and occupies a great portion of the porous structure, the pores are sometimes not uniform over the entire thickness of the vessel wall. However, if such non-uniformity does not impair the porosity, the pores are considered to be substantially uniform. Although the mean diameter of the cross section in the inside of the vessel wall of the pores is not particularly limited, it is preferably 1 to 100 μm, more preferably 3 to 75 μm since the mean diameter at the inner surface of the pores is 1 to 100 μm. When the mean diameter is more than 100 μm, the strength of the vessel wall is decreased or the porosity becomes too large. When the mean diameter is less than 1 μm, the porosity becomes poor or the compliance becomes too small.

In order to obtain the compliance approximate to that of the vital vessel, a density of the elastomer having a porous structure is from 0.05 to 0.3 g/cm$^3$, preferably from 0.1 to 0.25 g/cm$^3$, and more preferably from 0.1 to 0.2 g/cm$^3$.

The elastomer used in the present invention is a thermoplastic elastomer having a fine blood compatibility, i.e. an elastomer with an excellent antithrombogenicity which does not release any low molecular compound which causes acute poisoning, inflammation, hemolysis, fever and the like, and does not seriously impair the physiologic function of blood. Examples of such elastomers are, for instance, polystyrene elastomers, polyurethane elastomers, polyolefin elastomers, polyester elastomers, and the like. The above elastomers can be used in singly or as a mixture.

Since it is enough for the elastomer to have the characteristic of an elastomer only when it is formed into the artificial vessel, even a mixture of the above elastomer with a polymer not having the characteristic of an elastomer can be used as the elastomer in the present invention insofar as the final product has the characteristic of an elastomer.

Among the above elastomers, a polyether type segmented polyurethane, including segmented polyurethane urea, hereinafter referred to as the same, elastomers are more preferable from the viewpoint of strength, elongation, durability, antithrombogenicity and the like. A segmented polyurethane containing fluorine in a hard segment or a soft segment, and a segmented polyurethane disclosed in Japanese Unexamined Patent Publication (KOKAI) No. 211358/1982, which contains polydimethylsiloxane in its main chain are still more preferable. Particularly preferable elastomers are a segmented polyurethane which contains, in a part of the soft segment, polydimethylsiloxane having the formula:

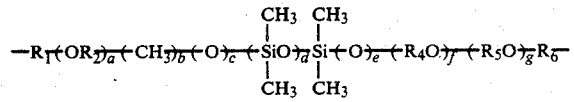

wherein each of $R_1$, $R_2$, $R_3$, $R_4$, $R_5$ and $R_6$ is an alkylene group having at least 1 carbon atom, preferably an alkylene group having 2 to 6 carbon atoms such as ethylene, propylene, butylene or hexamethylene; a and g are 0 or an integer of 1 to 30, b, c, e and f are 0 or 1, and d is an integer of not less than 2, preferably from 5 to 135.

Since the vessel wall of the artificial vessel of the present invention is made of the above-mentioned elastomer having a porous structure, the compliance can be made approximate to that of a vital vessel by controlling the ratio of the pore number based on the porous structure, the strength of the partition which forms the pores, the strength of the elastomer and the like.

A compliance of the vital vessel varies with the kind of vital vessel such as artery or vein, the diameter of the vessel and the like. Therefore, although the preferable compliance for the artificial vessel cannot be sweepingly determined since it varies with the diameter of the artificial vessel, the region to which the artificial vessel is applied, and the like, the artificial vessel of the present invention is prepared so as to have a compliance approximate to that of each vital vessel. Since the vital vessel where the usual vascular constructive surgery is carried out has the compliance of from about 0.1 to about 0.8, it is more preferable that the artificial vessel also has the compliance of this value. The compliance of the artificial vessel of the present invention can be controlled as previously mentioned, and thus the artificial vessel having any compliance value in a range of from 0.1 to 0.8 can be prepared. The artificial vessel having a compliance of from 0.1 to 0.8 can be used as arteries having a proper diameter. The artificial vessel having an inside diameter of from 1 to 6 mm and a compliance of from 0.1 to 0.5 can be preferably used as arteries of a small-caliber.

The "compliance" as used herein is defined by the equation (1):

$$C = \frac{\Delta V}{V_0 \cdot \Delta P} \times 100 \tag{1}$$

wherein C is the compliance, Vo is the volume of the measured vessel at the inner pressure of 50 mmHg, Δp is the pressure difference (100 mmHg) from 50 mmHg to 150 mmHg of the inner pressure, ΔV is the increasing volume of the vessel when the inner pressure rises from 50 mmHg to 150 mmHg. In practical measurement, a vessel is inserted into a closed circuit, and the volume of an injected liquid and the pressure variation in the circuit are measured by means of a microanalysis pump. From the results, the compliance can be calculated according to the above equation (1).

In case of the measurement of the artificial vessel having the porosity, communicating pores in the vessel wall are plugged by a procedure such as pre-clotting.

The artificial vessel of the present invention is made of an elastomer with an excellent blood compatibility, has the porosity and contact surface with blood suited for encapsulation and a compliance approximate to that of a vital vessel, and thus has an excellent patency. However, in order to prevent a rupture or an impairment which may occur due to an abnormally high pressure such as in case of surgery, or to maintain durability for a long period, the artificial vessel is preferably reinforced with tubular material made of fiber. Further, the artificial vessel is preferably reinforced with tubular material made of fiber so as to have a stress-strain curve approximate to that of a vital vessel.

Although the artificial vessel reinforced with tubular material made of fiber can be subjected to a sterilization procedure by gamma ray or ethylene oxide, it has a detect in that the artificial vessel shrinks in a sterilization procedure by boiling or by high-pressure steam. Therefore, in order to obtain the artificial vessel which does not shrink even in the sterilization procedure by boiling or by high-pressure steam, the artificial vessel is preferably reinforced with heat-set tubular material made of fiber.

The "heat-setting" procedure in the present invention is a procedure to heat the tubular material made of fiber to such a degree that the tubular material does not shrink in the sterilization procedure by boiling or by high-pressure steam, for example, at 121° C. for 20 minutes. In practice, the heat-setting procedure can be carried out by boiling, by exposing in steam, by maintaining a high temperature atmosphere, by conducting a sterilization by high-pressure steam, or the like. Among the above procedures, the heat-setting procedure is preferably carried out by the sterilization by high-pressure steam, which allows to conduct the heat-setting procedure surely and with a good operability.

The heat-set tubular material made of fiber in the present invention may be any of those prepared by heat-setting a fiber and then forming the fiber into a tubular material, by heat-setting a fiber, forming the fiber into a tubular material and further heat-setting the obtained tubular material, or by heat-setting a tubular material made of fiber itself. In viewpoint of operability, the heat-set tubular material made of fiber is preferably prepared by heat-setting a tubular material made of fiber itself.

The artificial vessel reinforced with the heat-set tubular material made of fiber is an artificial vessel where at least a part of the tubular material is in contact with and/or is combined with the porous material made of elastomer, and a mechanical interaction exists between the tubular material and the porous material made of elastomer in such a degree that both the tubular material and the porous material show nearly the same strain against blood pressure or stress applied from the outside.

The fiber used in the present invention is a fine and long fiber having a length not less than 100 times larger than its diameter, which is usually employed for producing a yarn, a net yarn, a rope, a woven fabric, a knitting fabric, a braid, a nonwoven fabric, or the like. The fiber may be made of an organic material or of an inorganic material, insofar as the fiber does not have any bad influence on a living body, the degradation of the fiber in a living body is negligible, and the fiber is stable in the sterilization procedure, and also the fiber can be formed into the tubular material. From the viewpoints of processability, commercial availability, pliability and uniformity, there are preferably employed a regenerated man-made fiber, a semi-synthetic fiber and a synthetic fiber. Examples of the fiber are, for instance, cellulose type fibers, protein type fibers, polyamide type fibers, polyester type fibers, polyurethane type fibers, polyethylene type fibers, polystyrene type fibers, polyvinylchloride type fibers, polyvinylidene chloride type fibers, polyfluoroethylene type fibers, polyacrylic type fibers, polyvinyl alcohol type fibers, and the like. Among them, a fiber having a stretching property is more preferably employed. Examples of such a stretch fiber are, for instance, fibers having a self-stretching property such as rubber type fibers, polyurethane elastic type fibers or polyester elastic type fibers; stretch bulked processed fibers such as Woolie nylon or Woolie Teflon; covered yarns prepared by winding another spun yarn or filament on an elongated rubber filament or a Spandex filament; and the like.

The tubular material made of fiber used in the present invention is a tubular material made of the above-mentioned fiber; a yarn spun from at least one of the above-mentioned fibers; a multifilament of at least one of the above-mentioned fibers; a woven fabric, a knit fabric, a braid, a nonwoven fabric or a fabric combined thereof, which are produced from the above fiber, yarn or multifiber, and the like. A tubular material made of a polyurethane foam of sponge like structure can also be employed.

The tubular material may be formed by fiber or material made of fiber by itself or by combining the fiber with the porous material made of elastomer so that the tubular structure is formed at the finishing. From the viewpoints of processability, workability and establishment of the stress-strain curve approximate to that of a vital vessel, there is preferably employed a tubular material made of a knit fabric of the fiber, more preferably a tubular material made of a knit fabric of stretch fiber.

The tubular material is not particularly limited to the above-mentioned materials insofar as the artificial vessel prepared by combining the tubular material with the porous material made of elastomer has a compliance and a stress-strain curve approximate to those of a vital vessel. Such properties of the tubular material can be achieved by, for instance, either of the following two processes or combination thereof. One process is to control the number of the connecting or contacting points of the fibers or yarns and to adjust the tightness of the connecting point of the fibers or yarns. Another process is to use a stretch fiber.

Although the stress-strain curve of a vital vessel cannot be sweepingly determined since it varies with the kind of vessel such as artery or vein, the diameter of a vessel and the like, a vital vessel substantially has the stress-strain curve (I) or (III) as shown in FIG. 2. The curves (I) and (III) are stress-strain curves of the carotid artery and of thoracic aorta, respectively. These stress-strain curves show that the elastic modulus, which is low at a normal blood pressure level, increase drastically when a stress over the normal blood pressure level is applied. As shown in FIG. 2, the stress-strain curve (II) of the artificial vessel of the present invention that of a vital vessel. The stress-strain curve can be measured with a tension testing machine usually employed in the polymer material field such as, for instance, Autograph AG-2000 made by Shimazu Coorporation.

A process for preparing the artificial vessel of the present invention is explained in the following description.

[Step 1]

An elastomer solution containing a pore-forming agent is coated on a mandrel and then dried.

[Step 2]

The same elastomer solution is further coated on the dried material in Step 1, which is then immersed into a coagulating liquid to deposit the elastomer.

[Step 3]

Step 2 is repeated, as occasion demands, to give a desired thickness, the mandrel is pulled out, and the pore-forming agent and the solvent are completely removed.

The artificial vessel of the present invention can be prepared by the above procedures. When the artificial vessel is reinforced with the tubular material made of fiber, the tubular material made of fiber is formed on the mandrel either in Step 1 or in Step 2, by covering the mandrel with the tubular material made of fiber, or by winding fiber or a strip made of fiber on the mandrel to form into a tubular structure.

The elastomer solution is prepared from three essential ingredients, i.e. an elastomer, a good solvent which can dissolve the elastomer, and a pore-forming agent.

Although a suitable good solvent cannot be sweepingly determined since it varies with the kind of elastomer, there can be employed solvents such as, for instance, N,N-dimethylacetamide, N,N-dimethylformamide, N-methyl-2-pyrolidone, dioxane, tetrahydrofuran, and the like, in a single form or as a mixture thereof.

The pore-forming agent used in the present invention can be any which is insoluble in the good solvent and can be removed from the tubular material after the preparation of the tubular material from the elastomer solution containing the pore-forming agent. For example, a common salt, calcium carbonate, glucose, starch, casein, collagen, gelatin, albumin and the like, having a particle size of from about 10 to about 74 μm, are suitably employed as the pore-forming agent.

The coagulating liquid used in the present invention can be any which is well miscible with the good solvent but does not dissolve the elastomer. For example, water, lower alcohols, ethylene glycol, propylene glycol, 1,4-butanediol, glycerin and the like, singly or as a mixture thereof, are employed as the coagulating liquid.

The thus prepared artificial vessel of the present invention has the porosity and contact surface with blood suited for encapsulation, and thus has an excellent patency. Also the artificial vessel has the compliance approximate to that of a vital vessel. When the artificial vessel is reinforced with the tubular material made of fiber, the stress-strain curve of the artificial vessel can be approximated to that of a vital vessel. Further, when the artificial vessel is reinforced with the heat-set tubular material made of fiber, the artificial vessel can be subjected to the sterilization procedure by boiling or by high-pressure steam.

In addition to the above properties, the artificial vessel of the present invention has other useful properties such that a surgical needle easily penetrates the artificial vessel and thus the vessel is easily sutured, that a bore formed by a needle can closes by itself, and that kinking cannot be formed in practical use where blood pressure is applied, since the vessel wall of the artificial vessel of the present invention substantially comprises the porous material made of the continuous elastomer.

Therefore, the artificial vessel of the present invention can be used as an artificial vessel, an artificial vessel for by-pass, a material for a patch, in vascular reconstruction surgery of vital vessel, and moreover, a blood access. Especially, the artificial vessel of the present invention is preferably used as an artificial artery having a compliance of from 0.1 to 0.8. Also, the artificial vessel of the present invention can be used as an artificial artery of small caliber having an inner diameter of from about 1 to about 6 mm and a compliance of from 0.1 to 0.5, which has not hitherto been available in clinical use. Thus, the artificial vessel of the present invention is preferably used in vascular reconstruction surgery of arteries below the knees and for by-pass between aorta and coronary. In addition, the artificial vessel of the present invention can also be used as an artificial soft vital tube such as an ureter.

The present invention is more particularly described and explained by means of the following Examples. It is to be understood that the present invention is not limited to the Examples and various changes and modifications may be made without departing from the scope of the present invention.

EXAMPLE 1

After synthesizing a pre-polymer with 27.35 parts (part by weight, as hereinafter) of 4,4'-diphenylmethane diisocyanate and 54.7 parts of polyoxytetramethylene glycol (molecular weight: 2000), the pre-polymer chain was extended with 4.75 parts of ethylene glycol and 13.2 parts of polydimethylsiloxane having polyethylene glycol at both ends (average molecular weight of polyethylene glycol at both ends: 681, average molecular weight of polydimethylsiloxane: 1040) to give a segmented polyurethane containing polydimethylsiloxane in the main chain.

The thus obtained polyurethane had a tensile strength of 350 kg/cm$^2$, an elongation of 670% and a critical surface tension calculated from a Zisman plot of 28 dyn/cm.

A mixed solvent of 45 ml of dioxane and 45 ml of N,N-dimethylacetamide was added to a mixture of 10 g of the above polyurethane and 10 g of casein having a mean particle size of from 20 to 30 μm, and the mixture was stirred. A glass rod having a diameter of 3 mm was immersed into the dispersion liquid and then taken out to coat the dispersion liquid on the glass rod, which was dried with hot wind at about 80° C.

After immersing the coated glass rod into the dispersion liquid, the glass rod which was further coated with the dispersion liquid was taken out and then immersed into water to deposit the elastomer. The above procedures were further repeated twice and the glass rod was pulled out to give a tubular material. The tubular material was then immersed into an aqueous solution of sodium hydroxide of pH 13 to remove casein with extraction and then washed with water to give an artificial vessel.

The obtained artificial vessel had an inner diameter of about 3 mm and an outer diameter of about 4.5 mm. From an observation with a scanning type electron microscope with magnification of about ×1000, there were about $6 \times 10^5/cm^2$ of circular to oval openings of pores having a mean diameter of from about 10 to about 15 μm and about $65 \times 10^5/cm^2$ of circular openings of holes having a mean diameter of from about 1 to about 2 μm on the inner surface. FIG. 1 shows an illustration of the observation with a scanning type electron microscope.

The artificial vessel was proved to have porosity by passing water through the vessel wall at a pressure of 120 mmHg, about 110 ml/min. of water penetrating to the outside per 1 cm² of the inner surface.

After pre-clotting bovine blood in the vessel and cutting the pre-clotted vessel to 8 cm, the artificial vessel was inserted into a closed circuit. The ACD bovine blood was fed into the closed circuit by a quantitative pump which fed 0.05 ml per stroke, and the change of the inner pressure was measured. The compliance provided to be 0.4 from calculation according to the equation (1) on the basis of the number of strokes and the change of the inner pressure.

The artificial vessel of about 7 cm in length was grafted to femoral artery of an adult mongrel dog. The grafted vessel showed patency for not less than two months.

The artificial vessel did not fray when cut at any point, and was excellent in suturing property. In addition, the bores of the surgical needle closed by themselves when the needle was removed. Further, the vessel tended not to form kinking under an inner pressure of from 50 to 150 mmHg.

From the above obtained results, it is clear that the artificial vessel has excellent properties as an artificial artery of small-caliber.

EXAMPLE 2

Before the last procedure of immersing the glass rod into the dispersion liquid in Example 1, a tubular material prepared by knitting Woolie polyester fiber of 50 deniers with a ribbon knitting machine of 24 needles was covered on the glass rod coated with the deposited elastomer. The procedure in Example 1 was otherwise repeated to prepare an artificial vessel reinforced with the tubular material made of fiber.

The obtained artificial vessel was observed as in Example 1 to prove that it had the same contact surface with blood as the artificial vessel prepared in Example 1. The compliance and penetration volume of water measured as in Example 1 were 0.3 and about 40 ml/cm², respectively. The artificial vessel had a stress-strain curve approximate to that of a vital vessel.

The patency of the artificial vessel was measured as in Example 1 and proved to be not less than two months.

EXAMPLE 3

A tubular material prepared by knitting Woolie polyester fiber of 50 deniers with a ribbon knitting machine was sterilized by high-pressure steam at 121° C. for 20 minutes and then dried. The procedure caused about 20% shrinkage of the tubular material.

Before the third procedure of immersing the glass rod into the dispersion liquid in Example 1, the above heat-set tubular material made of fiber was covered on the glass rod coated with the deposited elastomer. The covered glass rod was immersed into the above dispersion liquid and then taken out to coat the dispersion liquid on the surface of the covered glass rod, which was then immersed into water to deposit the elastomer. The glass rod was pulled out to give a tubular material. Afterwards, the procedure as in Example 1 was repeated to give an artificial vessel reinforced with the heat-set tubular material made of fiber.

The obtained artificial vessel was observed as in Example 1 to prove that it had the same contact surface with blood as the artificial vessel prepared in Example 1. The compliance and penetration volume measured as in Example 1 were 0.35 and about 50 ml/cm², respectively. The artificial vessel had a density of the vessel wall of 0.16 g/cm³ and a stress-strain curve approximate to that of a vital vessel as shown in FIG. 2.

The artificial vessel was sterilized by boiling at 100° C. for 30 minutes or by high-pressure steam at 121° C. for 20 minutes without any change in shape or size, which showed that the artificial vessel can be subjected to these sterilization procedures by boiling or by high-pressure steam.

The patency of the artificial vessel was measured as in Example 1 and proved to be not less than two months.

What I claim is:

1. An artificial vessel having high patency, wherein the vessel wall comprises an elastomer having a porous structure and a density of 0.1 to 0.25 g/cm³, and wherein the inner surface of the vessel wall has pores of a mean diameter of 1 to 100 μm and holes of a mean diameter of 0.1 to 5 μm, said pores in the inner surface of the vessel wall being in continuous communication with pores in the entire thickness of the vessel wall and pores on the outside surface of the vessel wall, said holes being concave depressions which do not penetrate the entire thickness of the vessel wall, wherein the proportion of the number of said pores in the inner surface of the vessel to the number of said holes in the inner surface of the vessel wall is 1/1 to 1/1,000.

2. The artificial vessel of claim 1, wherein the vessel is reinforced with tubular material made of fiber.

3. The artifical vessel of claim 1, wherein the vessel is reinforced with tubular material made of fiber, wherein said tubular material is heat-set prior to being incorporated into the vessel.

4. The artificial vessel of claim 1, wherein the elastomer is a segmented polyurethane urea.

5. The artificial vessel of claim 1, wherein the elastomer is a segmented polyurethane comprising a dimethylsiloxane of the formula

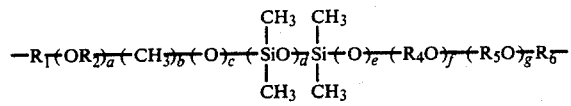
wherein each of $R_1$, $R_2$, $R_3$, $R_4$, $R_5$, and $R_6$ in an alkylene group having at least 1 carbon atoms, each of a and g is independently zero or an integer of 1 to 30, each of b, c, e and f is independently 0 or 1, and d is an integer of not less than 2.
* * * * *